US007074813B2

(12) United States Patent
Cai et al.

(10) Patent No.: US 7,074,813 B2
(45) Date of Patent: Jul. 11, 2006

(54) SUBSTITUTED N'-(ARYLCARBONYL)-BENZHYDRAZIDES, N'-(ARYLCARBONYL)-BENZYLIDENE-HYDRAZIDES AND ANALOGS AS ACTIVATORS OF CASPASES AND INDUCERS OF APOPTOSIS AND THE USE THEREOF

(75) Inventors: Sui Xiong Cai, San Diego, CA (US); Shailaja Kasibhatla, San Diego, CA (US); John Drewe, Carlsbad, CA (US); P. Sanjeeva Reddy, San Diego, CA (US); Han-Zhong Zhang, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 0 days.

(21) Appl. No.: 10/816,893

(22) Filed: Apr. 5, 2004

(65) Prior Publication Data

US 2004/0186078 A1 Sep. 23, 2004

Related U.S. Application Data

(62) Division of application No. 10/141,769, filed on May 10, 2002, now Pat. No. 6,716,859.

(60) Provisional application No. 60/289,803, filed on May 10, 2001.

(51) Int. Cl.
*A61K 31/44* (2006.01)
*C07D 213/643* (2006.01)
*C07D 213/69* (2006.01)
*C07D 213/70* (2006.01)

(52) U.S. Cl. ...................... 514/350; 514/348; 514/349; 546/286; 546/287; 546/296; 546/297; 546/298; 546/299

(58) Field of Classification Search ................ 546/286, 546/287, 288, 296, 297, 298, 299; 514/348, 514/349, 350
See application file for complete search history.

(56) References Cited

U.S. PATENT DOCUMENTS

| 5,281,619 | A | 1/1994 | Dell et al. |
|---|---|---|---|
| 5,741,818 | A | 4/1998 | Dimmock |
| 5,753,649 | A | 5/1998 | Tahara et al. |
| 5,981,531 | A | 11/1999 | Brewster et al. |
| 6,130,217 | A | 10/2000 | Arnold et al. |
| 6,225,323 | B1 | 5/2001 | Yatscoff et al. |
| 6,281,211 | B1 | 8/2001 | Cai et al. |
| 6,323,228 | B1 | 11/2001 | BaMaung et al. |
| 6,613,803 | B1 | 9/2003 | Wang et al. |
| 6,638,947 | B1 | 10/2003 | Wang et al. |
| RE38,425 | E | 2/2004 | Dimmock et al. |
| 6,696,442 | B1 | 2/2004 | Wang et al. |
| 2002/0061886 | A1 | 5/2002 | Wang et al. |
| 2002/0128292 | A1 | 9/2002 | Cai et al. |
| 2003/0045581 | A1 | 3/2003 | Cai et al. |
| 2003/0105140 | A1 | 6/2003 | Cai et al. |
| 2003/0225080 | A1 | 12/2003 | Wang et al. |

FOREIGN PATENT DOCUMENTS

WO    WO 00/07017    2/2000

OTHER PUBLICATIONS

Qian, X., and Zhang, R., "Synthesis and Insecticidal Activities of Novel 2,5-Disubstituted-1,3,4-oxadiazoles," *J. Chem. Technol. Biotechnol*. 67:124-130, Blackwell Scientific Publications (1996).

Database USPATFULL on STN Accession No. 2000:134884, (Pfizer Inc., New York, NY, USA), "Compounds enhancing antitumor activity of other cytotoxic agents," US Patent No. 6,130,217, Arnold et al., Oct. 10, 2000.

Database USPATFULL on STN Accession No. 1999:141938, (Zeneca Limited, London, United Kingdom) "Acid derivatives," US patent 5,981,531, Brewster et al., Nov. 9, 1999.

Database CHEMCATS on STN AN 1998:582475 (Catalog Name Maybridge HTS, Order No. BTB 03108), Chemical Name N'3-(2-aminobenzoyl)-2-phenoxypyridine-3-carbohydrazide (Apr. 3, 2000).

(Continued)

*Primary Examiner*—Patricia L. Morris
(74) *Attorney, Agent, or Firm*—Sterne, Kessler, Goldstein & Fox P.L.L.C.

(57) ABSTRACT

The present invention is directed to substituted N'-(arylcarbonyl)-benzhydrazides, N'-(arylcarbonyl)-benzylidene-hydrazides and analogs thereof, represented by the Formulae I and II:

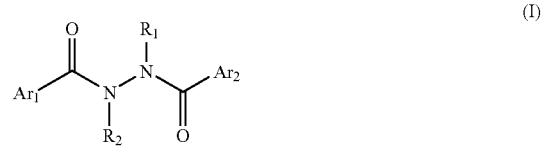

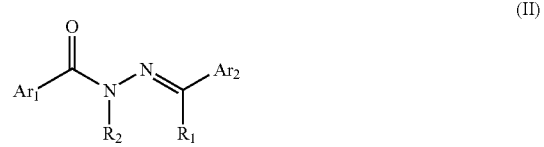

Figure 1A:
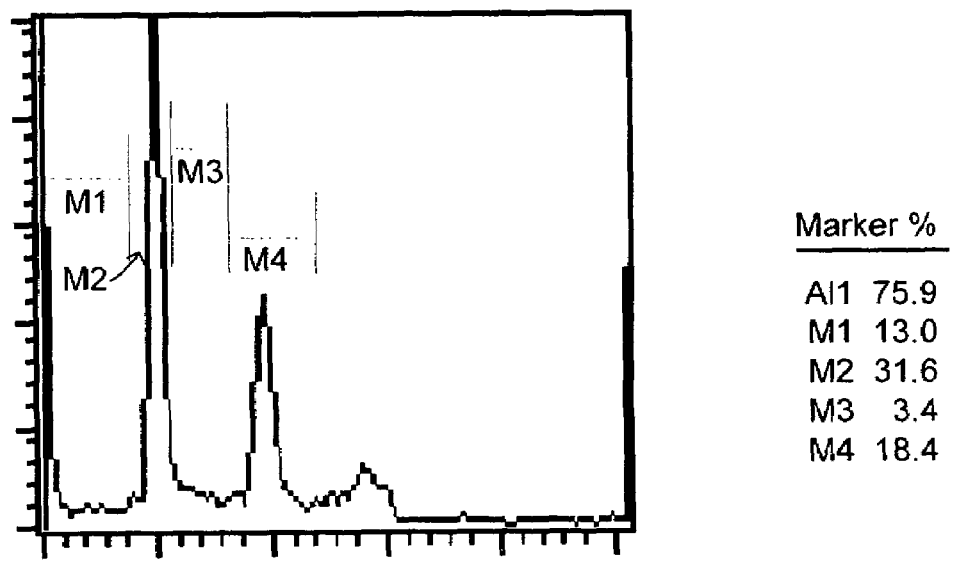

wherein $Ar_1$, $Ar_2$, and $R_1$–$R_2$ are defined herein. The present invention also relates to the discovery that compounds having Formulae I and II are activators of caspases and inducers of apoptosis. Therefore, the activators of caspases and inducers of apoptosis of this invention may be used to induce cell death in a variety of clinical conditions in which uncontrolled growth and spread of abnormal cells occurs.

10 Claims, 2 Drawing Sheets

OTHER PUBLICATIONS

Database CHEMCATS on STN AN 1998:582476 (Catalog Name Maybridge HTS, Order No. BTB 03109), Chemical Name N'3-[2-(methylamino)benzoyl]-2-phenoxypyridine-3-carbohydrazide (Apr. 3, 2000).

Database CHEMCATS on STN AN 1998:582469 (Catalog Maybridge, Order No. BTB 03099) Chemical Name N'3-(2-amino-5-nitrobenzoyl)-2-phenoxypyridine-3-carbohydrazide (Apr. 3, 2000).

Database CHEMCATS on STN AN 1998:582468 (Catalog Maybridge, Order No. BTB 03098) Chemical Name N'3-(2-amino-5-chlorobenzoyl)-2-phenoxypyridine-3-carbohydrazide (Apr. 3, 2000).

Database CHEMCATS on STN AN 1998:582456 (Catalog Maybridge, Order No. BTB 03075) Chemical Name N'3-[3-(trifluoromethyl)benzoyl]-2-phenoxypyridine-3-carbohydrazide (Apr. 3, 2000).

Database CHEMCATS on STN AN 1998:582454 (Catalog Maybridge, Order No. BTB 03073) Chemical Name N'3-(4-nitrobenzoyl)-2-phenoxypyridine-3-carbohydrazide (Apr. 3, 2000).

Database CHEMCATS on STN AN 1998:582455 (Catalog Maybridge, Order No. BTB 03074) Chemical Name N'3[(2-phenoxy-3-pyridyl)carbonyl]-2-phenoxypyridine-3-carbohydrazide (Apr. 3, 2000).

Database CHEMCATS on STN AN 1998:633657 (Catalog Name Maybridge HTS, Order No. BTB 03957), Chemical Name N'3-(2,6-diflurobenzoyl)-6-(4-chlorophenoxy)pyridine-3-carbohydrazide (May 30, 2002).

Database CHEMCATS on STN AN 1998:633656 (Catalog Maybridge HTS, Order No. BTB 03956) Chemical Name N'3-(4-chlorobenzoyl)-6-(4-chlorophenoxy)pyridine-3-carbohydrazide (May 30, 2002).

Marker %

Al1  75.9
M1  13.0
M2  31.6
M3   3.4
M4  18.4

Marker %

Al1  90.1
M1   9.0
M2  37.9
M3   4.8
M4  33.4

US 7,074,813 B2

SUBSTITUTED N'-(ARYLCARBONYL)-BENZHYDRAZIDES, N'-(ARYLCARBONYL)-BENZYLIDENE-HYDRAZIDES AND ANALOGS AS ACTIVATORS OF CASPASES AND INDUCERS OF APOPTOSIS AND THE USE THEREOF

BACKGROUND OF THE INVENTION

1. Field of the Invention

This invention is in the field of medicinal chemistry. In particular, the invention relates to optionally substituted N'-(arylcarbonyl)-benzhydrazides, N'-(arylcarbonyl)-benzylidene-hydrazides and analogs, and the discovery that these compounds are activators of caspases and inducers of apoptosis. The invention also relates to the use of these compounds as therapeutically effective anti-cancer agents.

2. Related Art

Organisms eliminate unwanted cells by a process variously known as regulated cell death, programmed cell death or apoptosis. Such cell death occurs as a normal aspect of animal development as well as in tissue homeostasis and aging (Glucksmann, A., *Biol. Rev. Cambridge Philos. Soc.* 26:59–86 (1951); Glucksmann, A., *Archives de Biologie* 76:419–437 (1965); Ellis, et al., *Dev.* 112:591–603 (1991); Vaux, et al., *Cell* 76:777–779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237:529–536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34). A cell activates its internally encoded suicide program as a result of either internal or external signals. The suicide program is executed through the activation of a carefully regulated genetic program (Wyllie, et al., *Int. Rev. Cyt.* 68.251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529–536 (1995)).

It has been found that a group of proteases are a key element in apoptosis (see, e.g., Thornberry, *Chemistry and Biology* 5:R97–R103 (1998); Thornberry, *British Med Bull.* 53:478–490 (1996)). Genetic studies in the nematode *Caenorhabditis elegans* revealed that apoptotic cell death involves at least 14 genes, two of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301–314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118–3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetimes. Normally, cells exist in a resting phase termed $G_o$. During multiplication, cells progress to a stage in which DNA synthesis occurs, termed S. Later, cell division, or mitosis occurs, in a phase called M. Antineoplastic drugs such as cytosine arabinoside, hydroxyurea, 6-mercaptopurine, and methotrexate are S phase specific, whereas antineoplastic drugs such as vincristine, vinblastine, and paclitaxel are M phase specific. Many slow growing tumors, for example colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (See, e.g., Hardman, et al., eds., *Goodman and Gilman's The Pharmacological Basis of Therapeutics*, Ninth Edition, McGraw-Hill, New York (1996), pp. 1225–1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Caspase cascade activators and inducers of apoptosis may also be a desirable therapy in the elimination of pathogens such as HIV, Hepatitis C and other viral pathogens. The long lasting quiecence followed by a disease progression may be explained by anti-apoptotic mechanism of these pathognes leading to persistent cellular reservoirs of the virions. It has been reported that HIV-1 infected T leukemia cells or peripheral blood mononuclear cells (PBMCs) underwent enhanced viral replication in the presence of caspase inhibitor Z-VAD-fmk. Furthermore, Z-VAD-fmk also stimulated endogenous virus production in activated PBMCs derived from HIV-1-infected asymptomatic individuals (Chinnaiyan, A. et. al. *Nature Medicine.* 3:333. 1997). Therefore apoptosis may serve as a beneficial host mechanism to limit HIV spread and new therapeutics using caspase/apoptosis activators may be useful to clear viral reservoirs from the infected individuals. Similarly, HCV infection also triggers anti-apoptotic mechanisms to evade host's immune surveillance leading to viral persistence and hepatocarcinogenesis (Tai D I et. al. Hepatology 3: 656–64, 2000). Therefore apoptosis inducers may be useful as therapeutics for HCV and other infectious disease. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

The present invention is related to the discovery that optionally substituted N'-(arylcarbonyl)-benzhydrazides, N'-(arylcarbonyl)-benzylidene-hydrazides and analogs, as represented in Formulae I and II, are activators of the caspase cascade and inducers of apoptosis. Thus, an aspect of the present invention is directed to the use of compounds of Formulae I and II as inducers of apoptosis.

The compounds of the present invention are represented by Formulae I and II:

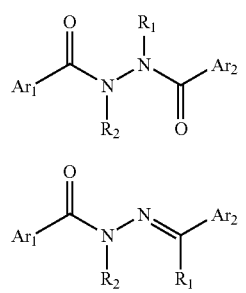

or pharmaceutically acceptable salts or prodrugs thereof, wherein:

$Ar_1$ is optionally substituted pyridyl, optionally substituted pyrimidinyl or optionally substituted phenyl;

$Ar_2$ is optionally substituted aryl or optionally substituted heteroaryl; and $R_1$ and $R_2$ are independently hydrogen, alkyl or cycloalkyl.

A second aspect of the present invention is to provide a method for treating, preventing or ameliorating neoplasia and cancer by administering a compound of one of the Formulae I and II to a mammal in need of such treatment.

Many of the compounds within the scope of the present invention are novel compounds. Therefore, a third aspect of the present invention is to provide novel compounds of Formulae I and II, and to also provide for the use of these novel compounds for treating, preventing or ameliorating neoplasia and cancer.

A fourth aspect of the present invention is to provide a pharmaceutical composition useful for treating disorders responsive to the induction of apoptosis, containing an effective amount of a compound of one of the Formulae I and II in admixture with one or more pharmaceutically acceptable carriers or diluents.

A fifth aspect of the present invention is directed to methods for the preparation of novel compounds of Formulae I and II.

BRIEF DESCRIPTION OF THE DRAWINGS/FIGURES

Figure 1B:
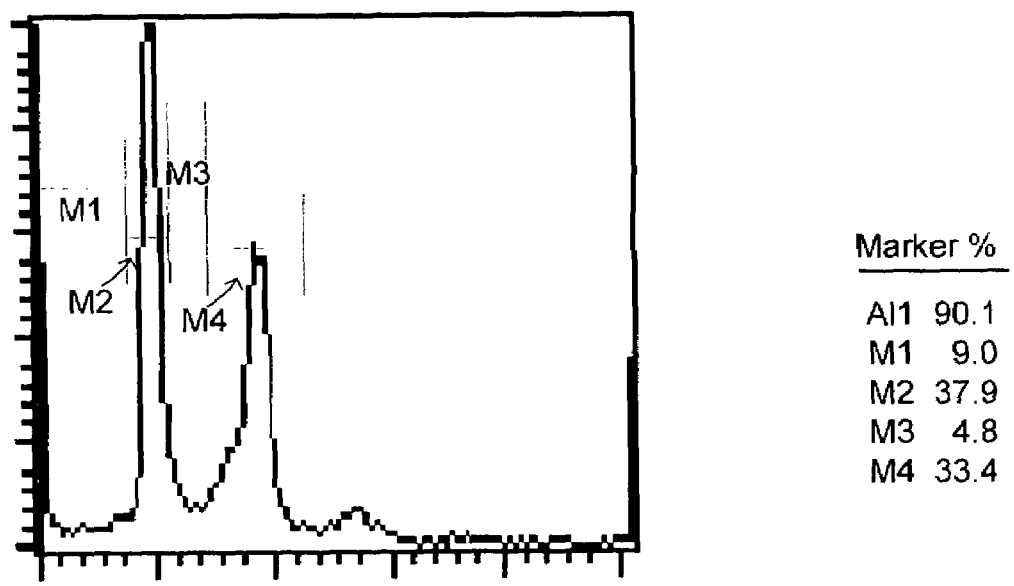

FIGS. 1A–B are graphs showing drug induced cell cycle arrest and apoptosis in T47D cells. FIG. 1A: control cells showing most of the cells in G1(M2). FIG. 1B: cells treated with 1 μM of N'-(2-phenoxypyridine-3-carbonyl)-3-(trifluoromethyl)benzhydrazide for 24 h showing an increase in the G2/M (M4) DNA content cells.

Figure 2:
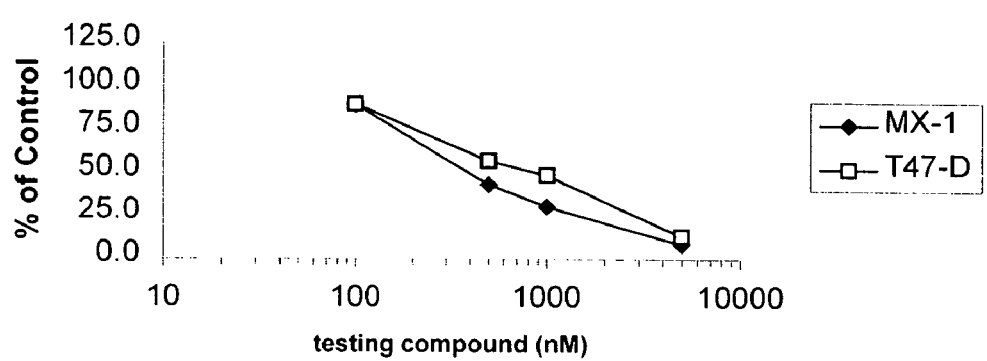

FIG. 2 is a graph showing inhibition of clonogenic survival of T47D and MX-1 cells treated for 48 h with different concentrations of N'-(2-phenoxypyridine-3-carbonyl)-3-(trifluoromethyl)benzhydrazide. FIG. 2 shows increasing inhibition of clonogenicity with increasing drug concentration, with $IC_{50}$ of about 1050 and 600 nM for T47D and MX-1 cells, respectively.

DETAILED DESCRIPTION OF THE INVENTION

The present invention arises out of the discovery that optionally substituted N'-(arylcarbonyl)-benzhydrazides, N'-(arylcarbonyl)-benzylidene-hydrazides and analogs, as represented in Formulae I and II, are potent and highly efficacious activators of the caspase cascade and inducers of apoptosis. Therefore compounds of Formulae I and II are useful for treating disorders responsive to induction of apoptosis.

Specifically, compounds useful in this aspect of the present invention are represented by Formulae I and II:

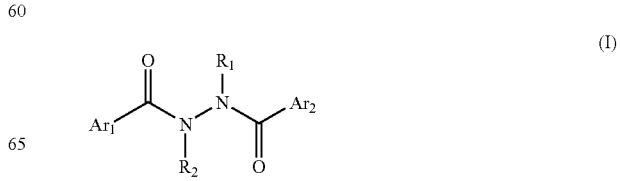

-continued

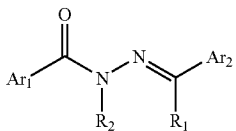
(II)

or pharmaceutically acceptable salts or prodrugs thereof, wherein:
$Ar_1$ is optionally substituted pyridyl, optionally substituted pyrimidinyl or optionally substituted phenyl;
$Ar_2$ is optionally substituted aryl or optionally substituted heteroaryl; and
$R_1$ and $R_2$ are independently hydrogen, alkyl or cycloalkyl.

Preferred compounds of Formulae I and II include compounds wherein $Ar_2$ is phenyl, naphthyl, pyridyl, quinolyl, isoquinolyl, thienyl, furyl or pyrrolyl, each of which is optionally substituted. Preferably $Ar_2$ is optionally substituted phenyl. Preferred compounds of Formulae I and II also include compounds wherein $R_1$ and $R_2$ are hydrogen.

Preferably, when $Ar_1$ is ((unsubstituted)phenoxy)pyridyl then $Ar_2$ is other than (i) phenyl which is substituted by $NH_2$, $NHCH_3$, $NO_2$, $C_1$ or $CF_3$ and (ii) (unsubstituted)phenoxypyridyl; and when $Ar_1$ is unsubstituted pyridyl, 6-chloropyrid-3-yl or 2-(2-trifluoroethoxy)pyrid-3-yl then $Ar_2$ is other than dichlorophenyl.

In a preferred embodiment of this invention, the compound is other than 4-hydroxybenzoic acid (2-hydroxybenzylidene)-hydrazide. Preferably, when the compound is of Formula II and $Ar_1$ is mono-substituted-4-phenyl then $Ar_2$ is other than mono-substituted-2-phenyl.

Preferably the compounds useful in this aspect of the present invention are represented by Formulae III and IV:

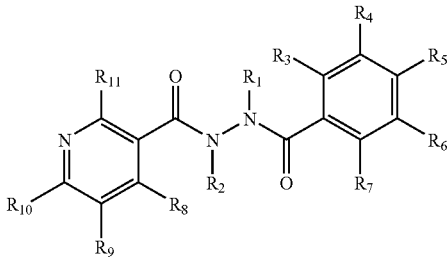
(III)

(IV)

or a pharmaceutically acceptable salt or prodrug thereof, wherein:
$R_1$ and $R_2$ are independently hydrogen, alkyl or cycloalkyl;
$R_3$–$R_{11}$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamino, hydroxy, thiol, sulfonyl, phosphonyl, acyloxy, azido, alkoxy, aryloxy, heteroaryloxy, arylalkoxy, heteroarylalkoxy, haloalkoxy, carboxy, carbonylamido or alkylthio, each of which is optionally substituted.

Preferably $R_1$ and $R_2$ are hydrogen. Preferably $R_{11}$ is optionally substituted hetereroaryloxy; more preferably, optionally substituted aryloxy; most preferably, optionally substituted phenoxy. In a preferred embodiment at least one of $R_3$–$R_7$ is other than hydrogen. In a preferred embodiment at least one of $R_3$–$R_7$ is hydroxy; more preferably, at least one of $R_3$ and $R_7$ is hydroxy.

Preferably:
(a) when each of $R_8$–$R_{10}$ is hydrogen and $R_{11}$ is unsubstituted phenoxy then

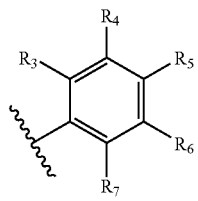

is other than phenyl which is substituted by $NH_2$, $NHCH_3$, $NO_2$, Cl or $CF_3$;
(b) when each of $R_8$–$R_{10}$ is hydrogen and $R_{11}$ is hydrogen or 2-trifluoroethoxy then

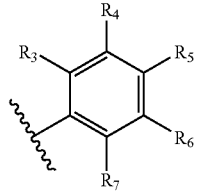

is other than dichlorophenyl; and
(c) when each of $R_8$, $R_9$ and $R_{11}$ is hydrogen and $R_{10}$ is chloro then

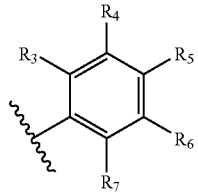

is other than dichlorophenyl.

More preferably, compounds useful in this aspect of the present invention are represented by Formulae V and VI:

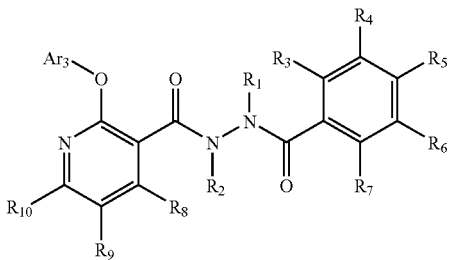

(V)

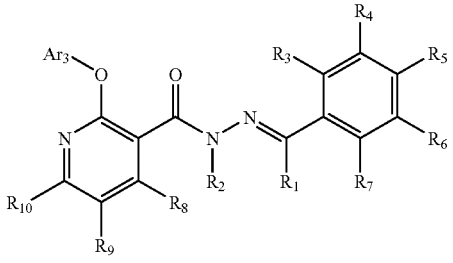

(VI)

or pharmaceutically acceptable salts or prodrugs thereof, wherein:

$Ar_3$ is optionally substituted aryl or optionally substituted heteroaryl;

$R_1$ and $R_2$ are independently hydrogen, alkyl or cycloalkyl;

$R_3$–$R_{10}$ are independently hydrogen, halo, haloalkyl, aryl, fused aryl, carbocyclic, a heterocyclic group, a heteroaryl group, alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, nitro, amino, cyano, acylamido, hydroxy, thiol, sulfonyl, phosphonyl, acyloxy, azido, alkoxy, aryloxy, arylalkoxy, haloalkoxy, carboxy, carbonylamido or alkylthiol.

Preferably $R_1$ and $R_2$ are hydrogen. Preferably $Ar_3$ is optionally substituted aryl; more preferably, optionally substituted phenyl; most preferably, substituted phenyl. In a preferred embodiment at least one of $R_3$–$R_7$ is other than hydrogen. In a preferred embodiment at least one of $R_3$–$R_7$ is hydroxy; more preferably, at least one of $R_3$ and $R_7$ is hydroxy.

Exemplary preferred compounds that may be employed in the method of the invention include, without limitation:

N'-(2-Phenoxypyridine-3-carbonyl)-4-nitrobenzhydrazide;
N'-(2-Phenoxypyridine-3-carbonyl)-2-amino-5-nitrobenzhydrazide;
N'-[5-(1-Hexynyl)pyridine-3-carbonyl]-3-(trifluoromethyl)-benzhydrazide;
N'-(Pyridine-3-carbonyl)-4-bromobenzhydrazide;
N'-[2-(4-Methylphenoxy)pyridine-3-carbonyl]-2-hydroxybenzhydrazide;
N'-(2-Phenoxypyridine-3-carbonyl)-3-(trifluoromethyl)benzhydrazide;
N'-[2-(4-Methylphenoxy)pyridine-3-carbonyl]-3-(trifluoromethyl)benzhydrazide;
N'-(2-Phenoxypyridine-3-carbonyl)-3-hydroxybenzhydrazide;
N'-(2-Phenoxypyridine-3-carbonyl)-(N-oxide-pyridine-3-carbonyl)hydrazide;
N'-(2-Phenoxypyridine-3-carbonyl)-3-aminobenzhydrazide;
N'-(2-Phenoxypyridine-3-carbonyl)-4-(trifluoromethyl)benzhydrazide;
N'-(2-Phenoxypyridine-3-carbonyl)-4-hydroxybenzhydrazide;
N'-(2-Phenoxypyridine-3-carbonyl)-2-hydroxybenzhydrazide;
N'-(2-Phenoxypyridine-3-carbonyl)-(pyridine-3-carbonyl)hydrazide;
N'-(2-Phenoxypyridine-3-carbonyl)-2-(trifluoromethyl)benzhydrazide;
N'-(2-Phenoxypyridine-3-carbonyl)-3-fluorobenzhydrazide;
N'-(2-Phenoxypyridine-3-carbonyl)-3-nitrobenzhydrazide;
N'-[2-(Methylthio)pyridine-3-carbonyl]-3-(trifluoromethyl)benzhydrazide;
N'-(2-Phenoxypyridine-3-carbonyl)-2-fluorobenzhydrazide;
2-Phenoxypyridine-3-carboxylic acid (3-trifluoromethyl-benzylidene)hydrazide;
2-Phenoxypyridine-3-carboxylic acid (2-trifluoromethyl-benzylidene)hydrazide;
2-Phenoxypyridine-3-carboxylic acid (4-trifluoromethyl-benzylidene)hydrazide;
2-Phenoxypyridine-3-carboxylic acid (4-hydroxybenzylidene)hydrazide;
2-Phenoxypyridine-3-carboxylic acid (3-pyridylmethylidene)hydrazide; and
2-Phenoxypyridine-3-carboxylic acid (4-pyridylmethylidene)hydrazide;
2-Chloropyridine-3-carboxylic acid (3-trifluoromethyl-benzylidene)hydrazide;
2-Anilinopyridine-3-carboxylic acid (3-trifluoromethyl-benzylidene)hydrazide;
2-(Pyridin-3-yloxy)-pyridine-3-carboxylic acid (3-trifluoromethyl-benzylidene)hydrazide;
Biphenyl-2-carboxylic acid (3-trifluoromethyl-benzylidene)hydrazide;
2-(3-Trifluoromethyl-anilino)-pyridine-3-carboxylic acid (3-trifluoro-methyl-benzylidene)hydrazide;
3,4,5-Trimethoxy-benzoic acid (3-trifluoromethyl-benzylidene)hydrazide;
3,4-Dihydroxy-benzoic acid (3-trifluoromethyl-benzylidene)hydrazide;
4-(Pyridin-4-yl)-2-(pyridin-2-yl)pyrimidine-5-carboxylic acid (3-trifluoromethyl-benzylidene)hydrazide;
5-Amino-2-phenoxy-benzoic acid (3-trifluoromethyl-benzylidene)hydrazide;
2-(Morpholin-4-ylmethyl)-benzoic acid (3-trifluoromethyl-benzylidene)hydrazide;
5-Nitro-2-phenoxy-benzoic acid (3-trifluoromethyl-benzylidene)hydrazide;
2-[1-(6-Chloro-pyridin-2-yl)-1H-[1,2,4]triazol-3yl-methoxy]-benzoic acid (3-trifluoromethyl-benzylidene)hydrazide;
2-Phenoxypyridine-3-carboxylic acid (3,5-bis(trifluoromethyl)-benzylidene)hydrazide;
2-Phenoxypyridine-3-carboxylic acid (3-methyl-benzylidene)hydrazide;
2-Phenoxypyridine-3-carboxylic acid (2-hydroxybenzylidene)hydrazide;
2-Phenoxypyridine-3-carboxylic acid benzylidene-hydrazide;
2-Phenoxypyridine-3-carboxylic acid (2,5-bis(trifluoromethyl)benzylidene)hydrazide;
2-Phenoxypyridine-3-carboxylic acid (3-trifluoromethoxy-benzylidene)hydrazide;
2-Phenoxypyridine-3-carboxylic acid (3-chlorobenzylidene) hydrazide;
2-Phenoxypyridine-3-carboxylic acid (3,4-difluoro-5-trifluoromethylbenzylidene)hydrazide;

2-Phenoxybenzoic acid (3-trifluoromethylbenzylidene)hydrazide; and
2-Phenoxybenzoic acid (2-hydroxybenzylidene)hydrazide;

and pharmaceutically acceptable salts and prodrugs thereof.

The present invention is also directed to novel compounds within the scope of Formulae I–VI. Exemplary novel compounds of this invention include, without limitation:

N'-(2-Phenoxypyridine-3-carbonyl)-4-nitrobenzhydrazide;
N'-(2-Phenoxypyridine-3-carbonyl)-2-amino-5-nitrobenzhydrazide;
N'-[5-(1-Hexynyl)pyridine-3-carbonyl]-3-(trifluoromethyl)benzhydrazide;
N'-(Pyridine-3-carbonyl)-4-bromobenzhydrazide;
N'-[2-(4-Methylphenoxy)pyridine-3-carbonyl]-2-hydroxybenzhydrazide;
N'-(2-Phenoxypyridine-3-carbonyl)-3-(trifluoromethyl)benzhydrazide;
N'-[2-(4-Methylphenoxy)pyridine-3-carbonyl]-3-(trifluoromethyl)benzhydrazide;
N'-(2-Phenoxypyridine-3-carbonyl)-3-hydroxybenzhydrazide;
N'-(2-Phenoxypyridine-3-carbonyl)-(N-oxide-pyridine-3-carbonyl)hydrazide;
N'-(2-Phenoxypyridine-3-carbonyl)-3-aminobenzhydrazide;
N'-(2-Phenoxypyridine-3-carbonyl)-4-(trifluoromethyl)benzhydrazide;
N'-(2-Phenoxypyridine-3-carbonyl)-4-hydroxybenzhydrazide;
N'-(2-Phenoxypyridine-3-carbonyl)-2-hydroxybenzhydrazide;
N'-(2-Phenoxypyridine-3-carbonyl)-(pyridine-3-carbonyl)hydrazide;
N'-(2-Phenoxypyridine-3-carbonyl)-2-(trifluoromethyl)benzhydrazide;
N'-(2-Phenoxypyridine-3-carbonyl)-3-fluorobenzhydrazide;
N'-(2-Phenoxypyridine-3-carbonyl)-3-nitrobenzhydrazide;
N'-[2-(Methylthio)pyridine-3-carbonyl]-3-(trifluoromethyl)benzhydrazide;
N'-(2-Phenoxypyridine-3-carbonyl)-2-fluorobenzhydrazide;
2-Phenoxypyridine-3-carboxylic acid (3-trifluoromethyl-benzylidene)hydrazide;
2-Phenoxypyridine-3-carboxylic acid (2-trifluoromethyl-benzylidene)hydrazide;
2-Phenoxypyridine-3-carboxylic acid (4-trifluoromethyl-benzylidene)hydrazide;
2-Phenoxypyridine-3-carboxylic acid (4-hydroxybenzylidene)hydrazide;
2-Phenoxypyridine-3-carboxylic acid (3-pyridylmethylidene)hydrazide; and
2-Phenoxypyridine-3-carboxylic acid (4-pyridylmethylidene)hydrazide;
2-Chloropyridine-3-carboxylic acid (3-trifluoromethyl-benzylidene)hydrazide;
2-Anilinopyridine-3-carboxylic acid (3-trifluoromethyl-benzylidene)hydrazide;
2-(Pyridin-3-yloxy)-pyridine-3-carboxylic acid (3-trifluoromethyl-benzylidene)hydrazide;
Biphenyl-2-carboxylic acid (3-trifluoromethyl-benzylidene)hydrazide;
2-(3-Trifluoromethyl-anilino)-pyridine-3-carboxylic acid (3-trifluoro-methyl-benzylidene)hydrazide;
3,4,5-Trimethoxy-benzoic acid (3-trifluoromethyl-benzylidene)hydrazide;
3,4-Dihydroxy-benzoic acid (3-trifluoromethyl-benzylidene)hydrazide;
4-(Pyridin-4-yl)-2-(pyridin-2-yl)pyrimidine-5-carboxylic acid (3-trifluoromethyl-benzylidene)hydrazide;
5-Amino-2-phenoxy-benzoic acid (3-trifluoromethyl-benzylidene)hydrazide;
2-(Morpholin-4-ylmethyl)-benzoic acid (3-trifluoromethyl-benzylidene)hydrazide;
5-Nitro-2-phenoxy-benzoic acid (3-trifluoromethyl-benzylidene)hydrazide;
2-[1-(6-Chloro-pyridin-2-yl)-1H-[1,2,4]triazol-3ylmethoxy]-benzoic acid (3-trifluoromethyl-benzylidene)hydrazide;
2-Phenoxypyridine-3-carboxylic acid (3,5-bis(trifluoromethyl)-benzylidene)hydrazide;
2-Phenoxypyridine-3-carboxylic acid (3-methyl-benzylidene)hydrazide;
2-Phenoxypyridine-3-carboxylic acid (2-hydroxylbenzylidene)hydrazide;
2-Phenoxypyridine-3-carboxylic acid benzylidene-hydrazide;
2-Phenoxypyridine-3-carboxylic acid (2,5-bis(trifluoromethyl)-benzylidene)hydrazide;
2-Phenoxypyridine-3-carboxylic acid (3-trifluoromethoxy-benzylidene)hydrazide;
2-Phenoxypyridine-3-carboxylic acid (3-chlorobenzylidene)hydrazide;
2-Phenoxypyridine-3-carboxylic acid (3,4-difluoro-5-trifluoromethyl-benzylidene)hydrazide;
2-Phenoxybenzoic acid (3-trifluoromethylbenzylidene)hydrazide; and
2-Phenoxybenzoic acid (2-hydroxybenzylidene)-hydrazide;

and pharmaceutically acceptable salts and prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2–10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2–10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include —NH$_2$, —NHR$_{15}$ and —NR$_{15}$R$_{16}$, wherein R$_{15}$ and R$_{16}$ are $C_{1-10}$ alkyl, cycloalkyl or optionally substituted aryl groups, or R$_{15}$ and R$_{16}$ are combined with the N to form a ring structure, such as a piperidine, or R$_{15}$ and R$_{16}$ are combined with the N and other group to form a ring, such as a piperazine. The alkyl group may be optionally substituted.

Optional substituents on the alkyl, alkoxy, alkenyl and alkynyl groups include one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl ($C_2$–$C_6$)alkenyl, $C_6$–$C_{10}$ aryl($C_2$–$C_6$)alkynyl, saturated and unsaturated heterocyclic or heteroaryl.

Optional substituents on the aryl, aralkyl, aralkenyl, aralkynyl and heteroaryl groups include one or more halo, $C_1$–$C_6$ haloalkyl, $C_6$–$C_{10}$ aryl, $C_6$–$C_{10}$ aryloxy, $C_4$–$C_7$ cycloalkyl, $C_1$–$C_6$ alkyl, $C_2$–$C_6$ alkenyl, $C_2$–$C_6$ alkynl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynly, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy or carboxy.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "aralkyl" is used herein to mean any of the above-mentioned $C_{1-10}$ alkyl groups substituted by any of the above-mentioned $C_{6-14}$ aryl groups. Preferably the arylakyl group is benzyl, phenethyl or naphthylmethyl.

The term "aralkenyl" is used herein to mean any of the above-mentioned $C_{2-10}$ alkenyl groups substituted by any of the above-mentioned $C_{6-14}$ aryl groups.

The term "aralkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, 2-oxobenzimidazolyl and 1H-[1,2,4]triazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate and oxalate; and inorganic and organic base addition salts with bases such as sodium hydroxy, Tris(hydroxymethyl)aminomethane (TRIS, tromethane) and N-methyl-glucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-6}$ dioic acid or anhydride thereof such as succinic and fumaric anhydrides according to methods known in the art); imines of amino containing compounds (e.g., those obtained by condensation with a $C_{1-4}$ aldehyde or ketone according to methods known in the art); carbamate of amino containing compounds such as those described by Leu, et. al., (*J. Med. Chem.* 42:3623–3628 (1999)) and Greenwald, et. al., (*J. Med. Chem.* 42:3657–3667 (1999)); acetals and ketals of alcohol containing compounds (e.g., those obtained by condensation with chloromethyl methyl ether or chloromethyl ethyl ether according to methods known in the art); and phosphonato and phosphono compounds (e.g., those obtained by condensation with a phosphate ester, phosphoryl chloride, or phosphoric acid), which include pharmaceutically acceptable mono-basic and di-basic addition salts of the phosphono group, for example, organic bases such as amine bases, which include ammonia, piperidine and morpholine.

The compounds of this invention may be prepared using methods known to those skilled in the art, or the novel methods of this invention. Specifically, the compounds of this invention with Formulae I and III may be prepared as illustrated by the exemplary reaction in Scheme 1. Reaction of the substituted pyridine-3-carbonyl chloride with the substituted benzhydrazide in a base such as pyridine produced the product N'-(2-phenoxypyridine-3-carbonyl)-3-(trifluoromethyl)benzhydrazide.

Scheme 1

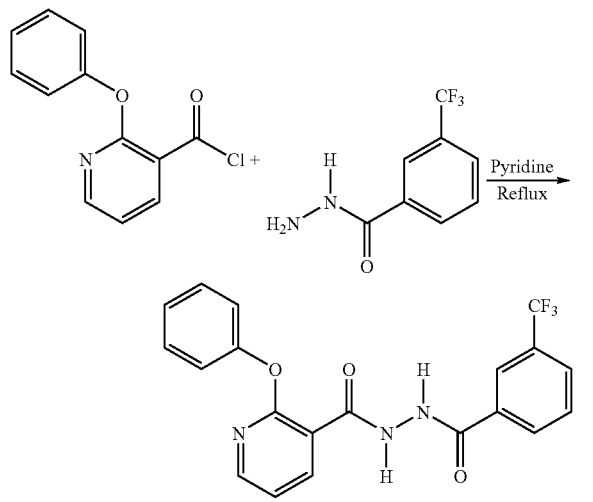

Alternatively, as shown in scheme 2, reaction of 2-phenoxy-nicotinic acid hydrazide with 3-trifluoromethyl-benzoyl chloride in the presence of a base such as pyridine produced N'-(2-phenoxypyridine-3-carbonyl)-3-(trifluoromethyl)benzhydrazide as the product.

Scheme 2

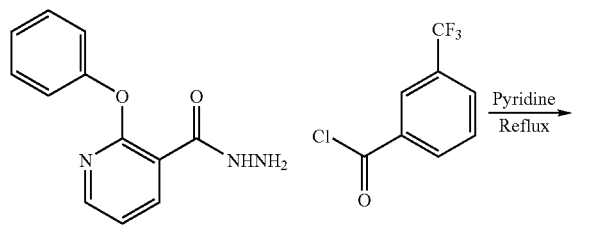

-continued

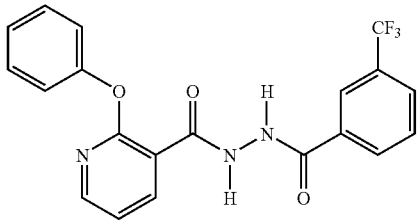

Compounds of this invention with Formulae II, IV and VI may be prepared as illustrated by the exemplary reaction in Scheme 3. Condensation of 2-phenoxy-nicotinic acid hydrazide with 3-trifluoromethylbenzaldehyde produced the product N'-(2-phenoxypyridine-3-carbonyl)-3-(trifluoromethyl)benzylidene-hydrazide.

Scheme 3

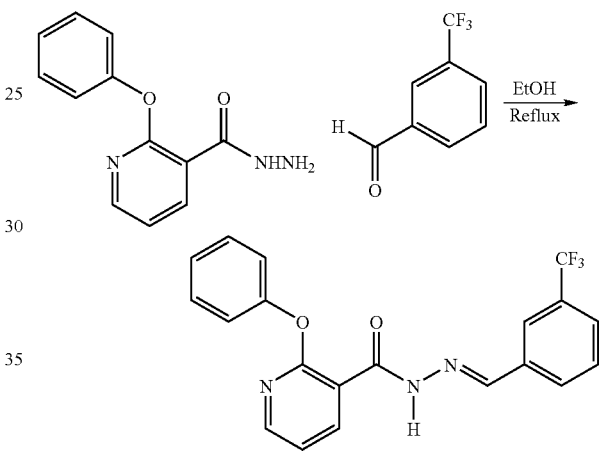

An important aspect of the present invention is the discovery that compounds having Formulae I–VI are activators of caspases and inducers of apoptosis. Therefore, these compounds are useful in a variety of clinical conditions in which there is uncontrolled cell growth and spread of abnormal cells, such as in the case of cancer.

Another important aspect of the present invention is the discovery that compounds having Formulae I–VI are potent and highly efficacious activators of caspases and inducers of apoptosis in drug resistant cancer cells, such as breast and prostate cancer cells, which enables these compounds to kill these drug resistant cancer cells. In comparison, most standard anti-cancer drugs are not effective in killing drug resistant cancer cells under the same conditions. Therefore, compounds of this invention are useful for the treatment of drug resistant cancer such as breast cancer in animals.

The present invention includes a therapeutic method useful to modulate in vivo apoptosis or in vivo neoplastic disease, comprising administering to a subject in need of such treatment an effective amount of a compound, or a pharmaceutically acceptable salt or prodrug of the compound of Formulae I–VI, which functions as a caspase cascade activator and inducer of apoptosis.

The present invention also includes a therapeutic method comprising administering to an animal an effective amount of a compound, or a pharmaceutically acceptable salt or prodrug of said compound of Formulae I–VI, wherein said therapeutic method is useful to treat cancer, which is a group of diseases characterized by the uncontrolled growth and spread of abnormal cells. Such diseases include, but are not limited to, Hodgkin's disease, non-Hodgkin's lymphomas, acute lymphocytic leukemia, chronic lymphocytic leukemia, multiple myeloma, neuroblastoma, breast carcinomas, ovarian carcinomas, lung carcinomas, Wilms' tumor, cervical carcinomas, testicular carcinomas, soft-tissue sarcomas, primary macroglobulinemia, bladder carcinomas, chronic granulocytic leukemia, primary brain carcinomas, retinoblastoma, glioma, malignant melanoma, small-cell lung carcinomas, stomach carcinomas, colon carcinomas, malignant pancreatic insulinoma, malignant carcinoid carcinomas, choriocarcinomas, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

In another embodiment, a pharmaceutical composition comprising a compound, or a pharmaceutically acceptable salt of said compound of Formulae I–VI, which functions as a caspase cascade activator and inducer of apoptosis in combination with a pharmaceutically acceptable vehicle is provided.

Another embodiment of the present invention is directed to a composition effective to inhibit neoplasia comprising a compound, or a pharmaceutically acceptable salt or prodrug of said compound of Formulae I–VI, which functions as a caspase cascade activator and inducer of apoptosis, in combination with at least one known cancer chemotherapeutic agent, or a pharmaceutically acceptable salt of said agent. Examples of known cancer chemotherapeutic agents which may be used for combination therapy include, but are not limited to alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as Herceptin® or Rituxan®. Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

Another embodiment of the present invention is directed to a composition effective to inhibit neoplasia comprising a bioconjugates of said compound of Formulae I–VI, which functions as a caspase cascade activator and inducer of apoptosis, in bioconjugation with at least one known therapeutically useful antibody, such as Herceptin® or Rituxan®, growth factors such as DGF, NGF, cytokines such as IL-2, IL-4, or any molecule that binds to the cell surface. The antibodies and other molecules will deliver the compound of Formulae I–VI to its targets and make it an effective anticancer agent. The bioconjugates could also enhance the anticancer effect of therapeutically useful antibodies, such as Herceptin® or Rituxan®.

Similarly, another embodiment of the present invention is directed to a composition effective in inhibiting neoplasia comprising a compound, or a pharmaceutically acceptable salt or prodrug of said compound of Formulae I–VI, which functions as a caspase cascade activator and inducer of apoptosis, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of said compound of Formulae I–VI, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13–21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133: 629–633 (1998) and Vaishnaw, A. K., et al., *J. Clin. Invest.* 103:355–363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475–483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5–21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603–608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42–48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer such as bisindolylmaleimide VIII may be therapeutically useful for the more effective elimination of detrimental cells and inhibition of T cell-mediated autoimmune diseases. Therefore an effective amount of a compound, or a pharmaceutically acceptable salt or prodrug of the compound of Formulae I–IV, which functions as a caspase cascade activator and inducer of apoptosis, should be an effective treatment for autoimmune diseases.

Psoriasis is a chronic skin disease that is characterized by scaly red patches. Psoralen plus ultraviolet A (PUVA) is a widely used and effective treatment for psoriasis vulgaris and Coven, et al., *Photodermatol. Photoimmunol. Photomed.* 15:22–27 (1999), reported that lymphocytes treated with psoralen 8-MOP or TMP and UVA, displayed DNA degradation patterns typical of apoptotic cell death. Ozawa, et al., *J. Exp. Med* 189:711–718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240–245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I–VI, which functions as a caspase cascade activator and inducer of apoptosis, should be an effective treatment for psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114: 119–128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I–IV, which functions as a caspase cascade activator and inducer of apoptosis, would be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J Leukoc. Biol.* 61:375–380 (1997)). Boirivant, et al., *Gastroenterology* 116: 557–565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I–VI, which functions as a caspase cascade activator and inducer of apoptosis, would be an effective treatment for inflammation.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated for apoptosis-mediated disorders. Preferably, about 0.01 to about 10 mg/kg of body weight is orally administered to treat or prevent such disorders. For intramuscular injection, the dose is generally about one-half of the oral dose. For example, a suitable intramuscular dose would be about 0.0025 to about 25 mg/kg of body weight, and most preferably, from about 0.01 to about 5 mg/kg of body weight. If a known cancer chemotherapeutic agent is also administered, it is administered in an amount that is effective to achieve its intended purpose. The amounts of such known cancer chemotherapeutic agents effective for cancer are well known to those of skill in the art.

The unit oral dose may comprise from about 0.01 to about 50 mg, preferably about 0.1 to about 10 mg of the compound of the invention. The unit dose may be administered one or more times daily as one or more tablets each containing from about 0.1 to about 10, conveniently about 0.25 to 50 mg of the compound or its solvates.

In a topical formulation, the compound may be present at a concentration of about 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which may be used pharmaceutically. Preferably, the preparations, particularly those preparations which may be administered orally and which may be used for the preferred type of administration, such as tablets, dragees, and capsules, and also preparations which may be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular apoptosis inducers of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular apoptosis inducers of the present invention with a solution of a pharmaceutically acceptable non-toxic base such as sodium hydroxide, potassium hydroxide, choline hydroxide, sodium carbonate, Tris, N-methyl-glucamine and the like.

The pharmaceutical compositions of the invention may be administered to any animal which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which may be used orally include push-fit capsules made of gelatin, as well as soft, sealed capsules made of gelatin and a plasticizer such as glycerol or sorbitol. The push-fit capsules may contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which may be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400), or cremophor, or cyclodextrins. Aqueous injection suspensions may contain substances which increase the viscosity of the suspension include, for example, sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

N'-(2-Phenoxypyridine-3-carbonyl)-3-(trifluoromethyl)benzhydrazide

A solution of 3-(trifluoromethyl)benzhydrazide (102.1 mg, 0.5 mmol), 2-phenoxypyridine-3-carbonyl chloride (117 mg, 0.5 mmol) in pyridine (5 mL) was refluxed for 2 h. It was evaporated in vacuo and the residue was purified by column chromatography (silica gel, EtOAc/$CH_2Cl_2$=4:1) to give 107 mg (54%) of the title compound. $^1$H NMR ($CDCl_3$): 10.88 (d, J=6.3 Hz, 1H), 9.80 (d, J=6.3 Hz, 1H), 8.60 (m, 1H), 8.30 (m, 1H), 8.17 (s, 1H), 8.06 (d, J=8.1 Hz, 1H), 7.81 (d, J=7.8 Hz, 1H), 7.61 (t, J=7.2 Hz, 1H), 7.51–7.46 (m, 2H), 7.34–7.17 (m, 4H).

EXAMPLE 2

N'-[2-(4-Methyl)phenoxypyridine-3-carbonyl]-3-(trifluoromethyl)benzhydrazide

The title compound was prepared similar to Example 1. From 3-(trifluoromethyl)benzhydrazide (51.1 mg, 0.25 mmol), 2-(4-methyl)phenoxypyridine-3-carbonyl chloride (62 mg, 0.25 mmol) was obtained 38 mg (37%) of the title compound. $^1$H NMR (acetone-$d_6$): 10.85 (bs, 1H), 10.00 (bs, 1H), 8.57 (m, 1H), 8.29 (m, 1H), 8.18 (s, 1H), 8.08 (d, J=8.1 Hz, 1H), 8.79 (d, J=7.8 Hz, 1H), 7.59 (t, J=7.5 Hz, 1H), 7.28–7.14 (m, 6H), 2.39 (s, 3H).

EXAMPLE 3

N'-(2-Phenoxypyridine-3-carbonyl)-3-hydroxybenzhydrazide

The title compound was prepared similar to Example 1. From 3-hydroxybenzhydrazide (152.2 mg, 1 mmol), 2-phenoxypyridine-3-carbonyl chloride (233.7 mg, 1 mmol) was obtained 228 mg (66%) of the title compound. $^1$H NMR (DMSO-$d_6$): 10.59 (s, 1H), 10.38 (s, 1H), 9.76 (s, 1H), 8.24 (m, 1H), 8.12 (m, 1H), 7.44–6.90 (m, 12H).

EXAMPLE 4

N'-(2-Phenoxypyridine-3-carbonyl)-(N-oxide-pyridine-3-carbonyl)hydrazide

The title compound was prepared similar to Example 1. From nicotinic acid hydrazide N-oxide (74 mg, 0.5 mmol), 2-phenoxypyridine-3-carbonyl chloride (116 mg, 0.5 mmol) was obtained 35 mg (20%) of the title compound. $^1$H NMR (acetone-$d_6$): 8.57 (bs,1H), 8.28 (d J=6.9 Hz, 2H), 7.97(bs, 2H), 7.38–7.03 (m, 7H), 6.86 (bs, 2H).

EXAMPLE 5

N'-(2-Phenoxypyridine-3-carbonyl)-3-aminobenzhydrazide

The title compound was prepared similar to Example 1. From 3-aminobenzhydrazide (151.2 mg, 1 mmol), 2-phenoxypyridine-3-carbonyl chloride (233.7 mg, 1 mmol) was obtained 12 mg (3.4%) of the title compound. $^1$H NMR (acetone-$d_6$): 10.95 (d, J=7.2 Hz, 1H), 9.33(d, J=6.9 Hz, 2H), 8.62 (m, 1H), 8.28 (m, 1H), 7.46 (t, J=8.4 Hz, 2H), 7.48–6.84 (m, 7H), 3.92 (bs, 2H).

EXAMPLE 6

N'-(2-Phenoxypyridine-3-carbonyl)-4-(trifluoromethyl)benzhydrazide

The title compound was prepared similar to Example 1. From 4-trifluoromethylbenzhydrazide (204.2 mg, 1 mmol), 2-phenoxypyridine-3-carbonyl chloride (233.7 mg, 1 mmol) was obtained 120 mg (30%) of the title compound. $^1$H NMR (acetone-$d_6$): 10.87 (d, J=6.9 Hz, 1H), 9.65(bs, 2H), 8.59 (m, 1H), 8.30 (m, 1H), 8.00 (t, J=8.4 Hz, 2H), 7.26 (d, J=8.4 Hz, 2H), 7.49 (t, J=7.2 Hz, 2H), 7.40–7.20 (m, 5H).

EXAMPLE 7

N'-(2-Phenoxypyridine-3-carbonyl)-4-hydroxybenzhydrazide

The title compound was prepared similar to Example 1. From 4-hydroxybenzhydrazide (152.2 mg, 1 mmol), 2-phenoxypyridine-3-carbonyl chloride (233.7 mg, 1 mmol) was obtained 48 mg (14%) of the title compound. $^1$H NMR (DMSO-$d_6$): 10.45 (s, 1H), 10.33 (s, 1H), 10.13 (bs, 1H), 8.24 (m, 1H), 8.15 (m, 1H), 7.80 (d, J=6.9 Hz, 2H), 7.44 (t, J=6.9 Hz, 2H), 7.26–7.18 (m, 4H), 6.84 (d, J=7.2 Hz, 2H).

EXAMPLE 8

N'-(2-Phenoxypyridine-3-carbonyl)-2-hydroxybenzhydrazide

The title compound was prepared similar to Example 1. From 2-hydroxybenzhydrazide (152.2 mg, 1 mmol), 2-phenoxypyridine-3-carbonyl chloride (233.7 mg, 1 mmol) was obtained 80 mg (23%) of the title compound. $^1$H NMR ($CD_3OD$): 8.43 (m, 1H), 8.22 (m, 1H), 7.94–7.88 (m, 2H), 7.48–7.40 (m, 3H), 7.30–7.22 (m, 3H), 6.98–6.91 (m, 2H).

EXAMPLE 9

N'-(2-Phenoxypyridine-3-carbonyl)-(pyridine-3-carbonyl)hydrazide

The title compound was prepared similar to Example 1. From nicotinic acid hydrazide (137.1 mg, 1 mmol), 2-phenoxypyridine-3-carbonyl chloride (233.7 mg, 1 mmol) was obtained 10 mg (3%) of the title compound. $^1$H NMR (CD$_3$OD): 9.10 (s, 1H), 8.73 (m, 1H), 8.50–8.16 (m, 4H), 7.62–7.10 (m, 6H).

EXAMPLE 10

N'-(2-Phenoxypyridine-3-carbonyl)-2-(trifluoromethyl)benzhydrazide

The title compound was prepared similar to Example 1. From 2-trifluoromethylbenzhydrazide (204.2 mg, 1 mmol), 2-phenoxypyridine-3-carbonyl chloride (233.7 mg, 1 mmol) was obtained 318 mg (80%) of the title compound. $^1$H NMR (CDCl$_3$): 10.70 (d, J=6.9 Hz, 1H), 9.19 (d, J=6.3 Hz, 1H), 8.49 (m, 1H), 8.28 (m, 1H), 7.63–7.26 (m, 9H), 7.16 (m, 1H).

EXAMPLE 11

N'-(2-Phenoxypyridine-3-carbonyl)-3-fluorobenzhydrazide

The title compound was prepared similar to Example 1. From 3-fluorobenzhydrazide (102.1 mg, 0.5 mmol), 2-phenoxypyridine-3-carbonyl chloride (116.7 mg, 0.5 mmol) was obtained 110 mg (55%) of the title compound. $^1$H NMR (CDCl$_3$): 10.70 (d, J=6.3 Hz, 1H), 9.19 (d, J=6.0 Hz, 1H), 8.45 (d, J=7.8 Hz, 1H), 8.28 (m, 1H), 7.80–7.10 (m, 10H).

EXAMPLE 12

N'-(2-Phenoxypyridine-3-carbonyl)-3-nitrobenzhydrazide

The title compound was prepared similar to Example 1. From 3-nitrobenzhydrazide (181.2 mg, 1 mmol), 2-phenoxypyridine-3-carbonyl chloride (233.7 mg, 1 mmol) was obtained 80 mg (21%) of the title compound. $^1$H NMR (CDCl$_3$): 10.85 (bs, 1H), 9.82 (bs, 1H), 8.76 (s, 1H), 8.62 (d, J=6 Hz, 1H), 8.41 (d, J=9.9 Hz, 1H), 8.30 (m, 1H), 8.23 (d, J=6.3 Hz, 1H), 7.72–7.19 (m, 7H).

EXAMPLE 13

N'-[2-(Methylthio)pyridine-3-carbonyl]-3-(trifluoromethyl)benzhydrazide

The title compound was prepared similar to Example 1. From 3-(trifluoromethyl)benzhydrazide (204.2 mg, 1 mmol), 2-(methylthio)nicotinoyl chloride (187.7 mg, 1 mmol) was obtained 208 mg (59%) of the title compound. $^1$H NMR (CDCl$_3$): 9.72 (bs, 1H), 9.67 (bs, 1H), 8.56 (m, 1H), 8.15 (s, 1H), 8.05 (d, J=7.2 Hz, 1H), 7.95 (d, J=6.9 Hz, 1H), 7.81 (d, J=7.2 Hz, 1H), 7.60 (t, J=7.8 Hz, 1H), 7.08 (q, 1H), 2.60 (s, 3H).

EXAMPLE 14

N'-(2-Phenoxypyridine-3-carbonyl)-2-fluorobenzhydrazide

The title compound was prepared similar to Example 1. From 2-fluorobenzhydrazide (154.2 mg, 1 mmol), 2-phenoxypyridine-3-carbonyl chloride (233.7 mg, 1 mmol) was obtained 97 mg (28%) of the title compound. $^1$H NMR (CDCl$_3$): 11.00 (bs, 1H), 9.90 (m, 1H), 8.64 (m, 1H), 8.29 (m, 1H), 8.20 (m, 1H), 7.60–7.20 (m, 9H).

EXAMPLE 15

2-Phenoxypyridine-3-carboxylic acid (3-trifluoromethylbenzylidene)hydrazide

A solution of 2-phenoxypyridine-3-carboxylic acid hydrazide (913 mg, 4 mmol), 3-trifluoromethylbenzaldehyde (696 mg, 4 mmol) in ethanol (40 mL) was refluxed for 13 h. It was cooled to room temperature and some precipitate was observed. The mixture was diluted by water (40 mL) and the solid was collected by filtration and washed with ethanol/water (1:1), dried to give 1.41 g (92%) of the title compound. $^1$H NMR (CDCl$_3$): 10.84 (s, 1H), 8.63 (m, 1H), 8.23 (s, 1H), 8.16 (m, 1H), 7.91 (bs, 1H), 7.88 (d, J=8.4 Hz, 1H), 7.54 (d, J=7.8 Hz, 1H), 7.40 (m, 3H), 7.24 (t, J=7.2 Hz, 1H), 7.18–7.08 (m, 3H).

EXAMPLE 16

2-Phenoxypyridine-3-carboxylic acid (2-trifluoromethyl-benzylidene)hydrazide The title compound was prepared similar to Example 15. From 2-phenoxypyridine-3-carboxylic acid hydrazide (57 mg, 0.25 mmol), 2-trifluoromethylbenzaldehyde (43 mg, 0.25 mmol) was obtained 82 mg (85%) of the title compound. $^1$H NMR (CDCl$_3$): 10.97 (s, 1H), 8.74 (d, J=7.8 Hz, 1H), 8.57 (s, 1H), 8.42 (d, J=7.8 Hz, 1H), 8.29 (m, 1H), 7.68 (d, J=7.2 Hz, 1H), 7.62 (t, J=7.5 Hz, 1H), 7.54–7.20 (m, 7H).

EXAMPLE 17

2-Phenoxypyridine-3-carboxylic acid (4-trifluoromethyl-benzylidene)hydrazide The title compound was prepared similar to Example 15. From 2-phenoxypyridine-3-carboxylic acid hydrazide (57 mg, 0.25 mmol), 4-trifluoromethylbenzaldehyde (43 mg, 0.25 mmol) was obtained 82 mg (85%) of the title compound. $^1$H NMR (CDCl$_3$): 10.98 (s, 1H), 8.74 (dd, J$_1$=7.8 Hz, J$_2$=2.1 Hz, 1H), 8.32 (s, 1H), 8.28 (m, 1H), 7.91 (d, J=8.1 Hz, 2H), 7.67 (d, J=8.1 Hz, 2H), 7.52 (t, J=8.4 Hz, 2H), 7.40–7.20 (m, 4H).

EXAMPLE 18

2-Phenoxypyridine-3-carboxylic acid (4-hydroxylbenzylidene)-hydrazide

The title compound was prepared similar to Example 15. From 2-phenoxypyridine-3-carboxylic acid hydrazide (57 mg, 0.25 mmol), 4-hydroxylbenzaldehyde (30 mg, 0.25 mmol) was obtained 65 mg (78%) of the title compound. $^1$H NMR (DMSO-d$_6$): 11.80 and 11.60 (1H), 9.90 (bs, 1H), 8.30–7.95 (m, 3H), 7.60–6.70 (m, 10H).

EXAMPLE 19

2-Phenoxypyridine-3-carboxylic acid (3-pyridylmethylidene)-hydrazide

The title compound was prepared similar to Example 15. From 2-phenoxypyridine-3-carboxylic acid hydrazide (57 mg, 0.25 mmol), 3-pyridinecarboxaldehyde (26 mg, 0.25 mmol) was obtained 65 mg (82%) of the title compound. $^1$H NMR (DMSO-$d_6$): 12.05 (bs, 1H), 8.90–7.80 (m, 6H), 7.50–7.00 (m, 7H).

EXAMPLE 20

2-Phenoxypyridine-3-carboxylic acid (4-pyridylmethylidene)-hydrazide

The title compound was prepared similar to Example 15. From 2-phenoxypyridine-3-carboxylic acid hydrazide (57 mg, 0.25 mmol), 4-pyridinecarboxaldehyde (26 mg, 0.25 mmol) was obtained 62 mg (78%) of the title compound. $^1$H NMR (DMSO-$d_6$): 12.15 (bs, 1H), 8.65 (d, J=4.8 Hz, 1H), 8.57 (d, J=5.1 Hz, 1H), 8.30–6.98 (m, 11H).

EXAMPLE 21

2-Chloropyridine-3-carboxylic acid (3-trifluoromethyl-benzylidene)-hydrazide

To a stirred solution of 2-chloro-nicotinoyl chloride (1.75 g, 10 mmol) in 40 mL THF was added 3-trifluoromethyl-benzylidene-hydrazine (1.88 g, 10 mmol) in 20 mL THF at 0° C., followed by 1.5 mL Et$_3$N. The solution was stirred at room temperature overnight and precipitate was observed. It was filtered and the solid was washed with MeOH, dried to yield the title compound (3.63 g, 90%). $^1$H NMR (acetone-$d_6$): 11.08 (s, 1H), 8.53 (d, J=4.5 Hz, 2H), 8.27 (s, 1H), 7.72 (m, 3H), 7.57 (m, 2H).

EXAMPLE 22

2-Anilinopyridine-3-carboxylic acid (3-trifluoromethyl-benzylidene)hydrazide

To a stirred solution of 2-anilino-nicotinic acid hydrazide (0.31 g, 1.05 mmol) in 20 mL EtOH was added 3-trifluoromethyl-benzaldehyde (0.182 g, 1.05 mmol) in 5 mL EtOH at room temperature. The mixture was refluxed for 4 h and cooled to room temperature, then diluted by 100 mL water. The precipitate was collected by filtration, washed with MeOH, and dried to yield the title compound (0.343 g, 85%). $^1$H NMR (acetone-$d_6$): 11.40 (S, 1H), 11.80 (S, 1H), 8.56 (s, 1H), 8.37 (d, J=4.8 Hz, 1H), 8.22 (d, J=8.1 Hz, 1H), 8.13 (s, 1H), 8.06 (d, J=8.1 Hz, 1H), 7.80 (m, 3H), 7.12 (m, 1H), 7.32 (m, 2H), 7.0 (t, J=8.1 Hz, 1H), 6.86 (q, J=4.5 Hz, 1H).

EXAMPLE 23

2-(Pyridin-3-yloxy)-pyridine-3-carboxylic acid (3-trifluoromethyl-benzylidene)-hydrazide To a stirred solution of 2-(pyridin-3-yloxy)-nicotinic acid (0.432 g, 2.0 mmol) in THF (15 mL) at 0° C. was added oxalylchloride (2 mL, 2M in CH$_2$Cl$_2$, 4.0 mmol) dropwise. The solution was stirred at room temperature for 3 h. The solvent was evaporated in vacuo to yield 2-(pyridin-3-yloxy)-nicotinoyl chloride as a solid. To a solution of 2-(pyridin-3-yloxy)-nicotinoyl chloride in 15 mL THF was added 3-trifluoromethyl-benzylidene-hydrazine (0.376 g, 2.0 mmol) in 5 mL THF and 1 mL Et$_3$N at 0° C. The reaction mixture was refluxed for 6 h and the solvent was evaporated. The residue was purified by chromatography with EtOAc: hexanes, 1:2, yielding (0.425 g, 55%) of the title compound. $^1$H NMR (DMSO-$d_6$): 12.20 (s, 1H), 8.70 (s, 1H), 8.37 (s, 1H), 8.24 (s, 1H), 8.21 (d, J=7.8 Hz, 1H), 8.01 (d, J=7.5 Hz, 1H), 7.90 (m, 2H), 7.78 (t, J=7.8 Hz, 1H), 7.41 (m, 2H), 6.43 (m, 2H).

EXAMPLE 24

Biphenyl-2-carboxylic acid (3-trifluoromethyl-benzylidene)-hydrazide

To a stirred solution of biphenyl-2-carboxylic acid-hydrazide (0.212 g, 1.0 mmol) in 20 mL EtOH was added 3-trifluoromethyl-benzaldehyde (0.174 g, 1.0 mmol) in 5 mL EtOH at room temperature. The mixture was refluxed for 4 h and cooled to room temperature, then was diluted by 100 mL of water. The precipitate was collected, washed with MeOH, and dried to yield the title compound (0.320 g, 87%). $^1$H NMR (acetone-$d_6$): 11.60 (s, 1H), 7.79 (s, 1H), 7.57 (s, 1H), 7.52 (d, J=12 Hz, 1H), 7.35 (d, J=12 Hz, 1H), 6.97~7.15 (m, 10H).

EXAMPLE 25

2-(3-Trifluoromethyl-anilino)-pyridine-3-carboxylic acid (3-trifluoromethyl-benzylidene)hydrazide The title compound was prepared from 2-(3-trifluoromethyl-phenylamino)-nicotinic acid-hydrazide and 3-trifluoromethyl-benzaldehyde by a procedure similar to Example 22. $^1$H NMR (DMSO-$d_6$): 12.30 (s, 1H), 10.58 (s, 1H), 8.53 (s, 1H), 8.45 (d, J=4.5 Hz, 1H), 8.31 (s, 1H), 8.24 (d, J=8.1 Hz, 1H), 8.12 (s, 1H), 8.06 (d, J=8.1 Hz), 7.84 (m, 3H), 7.54 (t, J=8.1 Hz, 1H), 7.30 (d, J=8.1 Hz, 1H), 7.03 (q, J=4.5 Hz, 1H).

EXAMPLE 26

3,4,5-Trimethoxy-benzoic acid (3-trifluoromethyl-benzylidene)-hydrazide

The title compound was prepared from 3,4,5-trimethoxy-benzoic acid hydrazide and 3-trifluoromethyl-benzaldehyde by a procedure similar to Example 22. $^1$H NMR (DMSO-$d_6$): 11.93 (s, 1H), 8.57 (s, 1H), 8.08 (s, 1H), 8.05 (d, J=8.1 Hz, 1H), 7.82 (d, J=7.5 Hz, 1H), 7.74 (d, J=7.5 Hz, 1H), 7.26 (s, 2H), 3.89 (s, 6H), 3.75 (s, 3H). MS (MH$^+$, MH$^-$): 451, 453.

EXAMPLE 27

3,4-Dihydroxy-benzoic acid (3-trifluoromethyl-benzylidene)-hydrazide

The title compound was prepared from 3,4-dihydroxy-benzoic acid hydrazide and 3-trifluoromethyl-benzaldehyde by a procedure similar to Example 22. $^1$H NMR (DMSO-$d_6$): 11.79 (s, 1H), 9.55 (s, 1H), 9.28 (s, 1H), 8.50 (s, 1H), 8.04 (s, 1H), 8.0 (d, J=7.8 Hz, 1H), 7.78 (d, J=7.8 Hz, 1H), 7.70 (d, J=8.4 Hz, 1H), 7.38 (d, J=2.4 Hz, 1H), 7.31 (d, J=8.1 Hz, 1H), 6.83 (d, J=8.4 Hz, 1H).

EXAMPLE 28

4-(Pyridin-4-yl)-2-(pyridin-2-yl)pyrimidine-5-carboxylic acid (3-trifluoromethyl-benzylidene)-hydrazide The title compound was prepared from 4-(pyridin-4-yl)-2-(pyridin-2-yl)pyrimidine-5-carboxylic acid-hydrazide and 3-trifluoromethyl-benzaldehyde by a procedure similar to Example 22. $^1$H NMR (DMSO-$d_6$): 12.38 (s, 1H), 9.30 (s, 1H), 9.22 (s, 1H), 8.84 (m, 1H), 8.78 (d, J=6.0 Hz, 1H), 8.68 (d, J=6.0 Hz, 1H), 8.54 (m, 1H), 8.31 (s, 1H), 8.01 (m, 2H), 7.97 (s, 1H), 7.82 (m, 1H), 7.73 (m, 1H), 7.62 (m, 2H).

EXAMPLE 29

5-Amino-2-phenoxy-benzoic acid (3-trifluoromethyl-benzylidene)-hydrazide

A mixture of phenol (5.64 g, 60 mmol) and potassium t-butoxide (6.74 g, 60 mmol) in 50 mL 1,4-dioxane was stirred at room temperature for 0.5 h. To the mixture was added 2-chloro-5-nitro-benzoic acid methyl ester (10.78 g, 50 mmol) and the mixture was refluxed overnight. The solvent was evaporated and the residue was purified by chromatography with EtOAc:hexanes, 1:4, as eluant, yielding (11.739 g, 86%) 5-nitro-2-phenoxy-benzoic acid methyl ester. A mixture of 5-nitro-2-phenoxy-benzoic acid methyl ester (2.0 g, 7.32 mmol) in 30 mL ethanol and Pd/C (200 mg) were hydrogenated at 40 psi overnight to yield 5-amino-2-phenoxy-benzoic acid methyl ester (1.672 g, 94%). A mixture of 5-amino-2-phenoxy-benzoic acid methyl ester (0.95 g, 3.9 mmol) and hydrazine (4 mL, 80%) was refluxed for 4 h to yield 5-amino-2-phenoxy-benzoic acid hydrazide (0.722 g, 76%). The title compound was prepared from 5-amino-2-phenoxy-benzoic acid hydrazide and 3-trifluoromethyl-benzaldehyde by a procedure similar to Example 22. $^1$H NMR (CDCl$_3$): 10.81 (s, 1H), 8.15 (s, 1H), 8.0 (s, 1H), 7.98 (d, J=7.5 Hz, 1H), 7.66 (s, 1H), 7.64 (d, J=7.5 Hz, 1H), 7.53 (t, J=7.2 Hz, 1H), 7.40 (m, 2H), 7.19 (t, J=7.5 Hz, 1H), 7.07 (d, J=7.8, 2H), 6.80 (m, 2H).

EXAMPLE 30

2-(Morpholin-4-ylmethyl)-benzoic acid (3-trifluoromethyl-benzylidene)hydrazide A solution of N-bromosuccinimide, dibromomethane (3.56 g, 20 mmol) and methyl-2-methylbenzoate (3.04 g, 20 mmol) in 30 mL CHCl$_3$ was refluxed for 4 h. The solvent was evaporated and the residue was purified by column chromatography, with EtOAc:hexanes, 1:5, as eluant, yielding (3.496 g, 76%) of 2-bromomethyl-benzoic acid methyl ester. A solution of 2-bromomethyl-benzoic acid methyl ester (368 mg, 2 mmol) and morpholine (174 mg, 2.0 mmol) in 8 mL DMF with 1 mL HCl (2 N) was refluxed overnight. The solvent was evaporated in vacuo and the residue was purified by column chromatography with EtOAc:hexanes, 1:4, yielding (180 mg, 38%) 2-(morpholin-4-ylmethyl)-benzoic acid methyl ester. The title compound was prepared from 2-(morpholin-4-ylmethyl)-benzoic acid methyl ester, hydrazine and then 3-trifluoromethyl-benzaldehyde in two steps by procedures similar to Example 29. $^1$H NMR (CDCl$_3$): 8.46 (s, 1H), 8.02 (m, 2H), 7.96 (d, J=7.8 Hz, 1H), 7.45 (d, J=7.8 Hz, 1H), 7.54 (d, J=7.8 Hz, 1H), 7.45 (m, 2H), 7.22 (m, 1H), 3.82 (t, J=4.8 Hz, 4H), 2.64 (t, J=4.8 Hz, 4H).

EXAMPLE 31

5-Nitro-2-phenoxy-benzoic acid (3-trifluoromethyl-benzylidene)-hydrazide

A mixture of 5-nitro-2-phenoxy-benzoic acid methyl ester (4.0 g, 14.7 mmol) and hydrazine (5 mL, 80%) was refluxed for 4 h to yield 5-nitro-2-phenoxy-benzoic acid hydrazide (2.97 g, 74%). The title compound was prepared from 5-nitro-2-phenoxy-benzoic acid hydrazide and 3-trifluoromethyl-benzaldehyde by a procedure similar to Example 22. $^1$H NMR (DMSO-$d_6$): 12.20 (s, 1H), 8.52 (s, 1H), 8.43 (s, 1H), 8.35 (d, J=7.2 Hz, 1H), 8.17 (s, 1H), 8.10 (d, J=6.6 Hz, 1H), 7.81 (m, 1H), 7.75 (t, J=6.6 Hz, 1H), 7.54 (t, J=7.2 Hz, 1H), 7.35 (m, 2H), 7.27 (d, J=7.2 Hz, 1H), 7.03 (m, 2H).

EXAMPLE 32

2-[1-(6-Chloro-pyridin-2-yl)-1H-[1,2,4]triazol-3yl-methoxy]-benzoic acid (3-trifluoromethyl-benzylidene)-hydrazide The title compound was prepared from 2-[1-(6-chloro-pyridin-2-yl)-1H-[1,2,4]triazol-3-ylmethoxy]-benzoic acid hydrazide and 3-trifluoromethyl-benzaldehyde by a procedure similar to Example 22. $^1$H NMR (DMSO-$d_6$): 11.92 (s, 1H), 8.43 (s, 1H), 8.0 (m, 3H), 7.80 (m, 3H), 7.70 (t, J=7.5 Hz, 1H), 7.60 (m, J=7.5 Hz, 1H), 7.45 (d, J=8.4 Hz, 1H), 7.17 (d, J=7.5 Hz, 1H 5.50 (s, 1H).

EXAMPLE 33

2-Phenoxypyridine-3-carboxylic acid (3,5-bis(trifluoromethyl)-benzylidene)hydrazide The title compound was prepared similar to Example 15. From 2-phenoxypyridine-3-carboxylic acid hydrazide (45.85 mg, 0.20 mmol), 3,5-bis(trifluoromethyl)benzaldehyde (48.42 mg, 0.20 mmol) was obtained 73 mg (81%) of the title compound. $^1$H NMR (CDCl$_3$): 11.05 (s, 1H), 8.75 (dd, J=7.8 Hz, 2.1 Hz, 1H), 8.51 (s, 1H), 8.30 (m, 1H), 8.24 (s, 2H), 7.89(s, 1H), 7.52 (t, J=7.2 Hz, 2H), 7.36 (t, J=7.5 Hz, 1H), 7.25–03 (m, 2H).

EXAMPLE 34

2-Phenoxypyridine-3-carboxylic acid (3-methyl-benzylidene)-hydrazide

The title compound was prepared similar to Example 15. From 2-phenoxypyridine-3-carboxylic acid hydrazide (45.85 mg, 0.20 mmol), 3-methylbenzaldehyde (24 mg, 0.20 mmol) was obtained 50 mg (76%) of the title compound. $^1$H NMR (CDCl$_3$): 10.95 (s, 1H), 8.75 (dd, J=7.8, 2.1 Hz, 1H), 8.27 (m, 1H), 8.19 (s, 1H), 7.71 (s, 1H), 7.51 (d, J=8.75 Hz, 2H), 7.38–7.20 (m, 5H), 2.38 (s, 3H).

EXAMPLE 35

2-Phenoxypyridine-3-carboxylic acid (2-hydroxylbenzylidene)-hydrazide

The title compound was prepared similar to Example 15. From 2-phenoxypyridine-3-carboxylic acid hydrazide (45.82 mg, 0.20 mmol), 2-hydroxylbenzaldehyde (24.4 mg, 0.20 mmol) was obtained 50 mg (75%) of the title compound. $^1$H NMR (CDCl$_3$): 11.11 (s, 1H), 10.78 (s, 1H), 8.73

(m, 1H), 8.42 (s, 1H), 8.28 (m, 1H), 7.58–7.48 (m, 2H), 7.40–6.98 (m, 7H), 6.85–6.95 (m, 1H).

EXAMPLE 36

2-Phenoxypyridine-3-carboxylic acid benzylidene-hydrazide

The title compound was prepared similar to Example 15. From 2-phenoxypyridine-3-carboxylic acid hydrazide (45.82 mg, 0.20 mmol), benzaldehyde (21.20 mg, 0.20 mmol) was obtained 46 mg (72%) of the title compound. $^1$H NMR (CDCl$_3$): 10.80 (bs, 1H), 8.78 (d, 1H), 8.26 (m, 1H), 8.24 (s, 1H), 7.80 (bs, 2H), 7.58–7.18 (m, 9H).

EXAMPLE 37

2-Phenoxypyridine-3-carboxylic acid (2,5-bis(trifluoromethyl)-benzylidene)hydrazide The title compound was prepared similar to Example 15. From 2-phenoxypyridine-3-carboxylic acid hydrazide (34.39 mg, 0.15 mmol), 2,5-bis(trifluoromethyl)benzaldehyde (36.30 mg, 0.15 mmol) was obtained 59 mg (87%) of the title compound. $^1$H NMR (CDCl$_3$): 11.00 (s, 1H), 8.75 (bs, 1H), 8.74 (m, 1H), 8.66 (s, 1H), 8.30 (m, 1H), 7.84–7.75 (m, 2H), 7.52 (t, J=7.2 Hz, 2H), 7.35 (t, J=7.8 Hz, 1H), 7.25–7.20 (m, 3H).

EXAMPLE 38

2-Phenoxypyridine-3-carboxylic acid (3-trifluoromethoxy-benzylidene)hydrazide

The title compound was prepared similar to Example 15. From 2-phenoxypyridine-3-carboxylic acid hydrazide (34.39 mg, 0.15 mmol), 3-trifluoromethoxybenzaldehyde (21 mg, 0.15 mmol) was obtained 52 mg (86%) of the title compound. $^1$H NMR (CDCl$_3$): 10.95 (s, 1H), 8.74 (q, 1H), 8.32 (s, 1H), 8.27 (q, 1H), 7.66–7.20 (m, 10H).

EXAMPLE 39

2-Phenoxypyridine-3-carboxylic acid (3-chlorobenzylidene)-hydrazide

The title compound was prepared similar to Example 15. From 2-phenoxypyridine-3-carboxylic acid hydrazide (34.39 mg, 0.15 mmol), 3-chlorobenzaldehyde (21 mg, 0.15 mmol) was obtained 49 mg (93%) of the title compound. $^1$H NMR (CDCl$_3$): 10.95 (s, 1H), 8.74 (q, 1H), 8.28 (q, 1H), 8.23 (s, 1H), 7.83 (s, 1H), 7.64–7.20 (m, 9H).

EXAMPLE 40

2-Phenoxypyridine-3-carboxylic acid (3,4-difluoro-5-trifluoromethyl-benzylidene)-hydrazide The title compound was prepared similar to Example 15. From 2-phenoxypyridine-3-carboxylic acid hydrazide (34.39 mg, 0.15 mmol), 3,4-difluoro-5-(trifluoromethyl) benzaldehyde (31.5 mg, 0.15 mmol) was obtained 48 mg (76%) of the title compound. $^1$H NMR (CDCl$_3$): 10.95 (s, 1H), 8.75 (q, 1H), 8.39 (s, 1H), 8.29 (q, 1H), 7.98–7.90 (m, 1H), 7.71 (d, J=5.4 Hz, 1H) 7.52 (m, 2H), 7.36 (m, 1H), 7.24–7.20 (m, 3H).

EXAMPLE 41

2-Phenoxybenzoic acid (3-trifluoromethylbenzylidene)-hydrazide

The title compound was prepared similar to Example 15. From 2-phenoxybenzoic acid hydrazide (456 mg, 2 mmol), 3-trifluoromethylbenzaldehyde (348 mg, 2 mmol) was obtained 632 mg (82%) of the title compound. $^1$H NMR (CDCl$_3$): 10.80 (s, 1H), 8.37(d, J=8.1 Hz, 1H), 8.27 (s, 1H), 7.99 (s, 1H), 7.98 (d, 1H), 7.63 (d, J=7.50 Hz, 1H), 7.58–7.13 (m, 8H), 6.85 (d, J=8.1 Hz, 1H).

EXAMPLE 42

2-Phenoxybenzoic acid (2-hydroxybenzylidene)-hydrazide

The title compound was prepared similar to Example 15. From 2-phenoxybenzoic acid hydrazide (456.5 mg, 2 mmol), 2-hydroxybenzaldehyde (244.3 mg, 2 mmol) was obtained 493 mg (74%) of the title compound. $^1$H NMR (CDCl$_3$): 11.16 (s, 1H), 10.65 (s, 1H), 8.37 (d, J=8.1 Hz, 1H), 8.34 (s, 1H), 7.52–6.80 (m, 12H).

EXAMPLE 43

Identification of N'-(2-Phenoxypyridine-3-carbonyl)-3-(trifluoromethyl)benzyhydrazide and Analogs as Caspase Cascade Activators and Inducers of Apoptosis in Solid Tumor Cells Human breast cancer cell lines T-47D and ZR-75-1 were grown according to media component mixtures designated by American Type Culture Collection+10% FCS (Invitrogen Corporation), in a 5% CO$_2$-95% humidity incubator at 37° C. T-47D and ZR-75-1 cells were maintained at a cell density between 50 and 80% confluency at a cell density of 0.1 to 0.6×10$^6$ cells/ml. Cells were harvested at 600×g and resuspended at 0.65×10$^6$ cells/ml into appropriate media+10% FCS. An aliquot of 45 µl of cells was added to a well of a 96-well microtiter plate containing 2.5 µl of a 10% DMSO in RPMI-1640 media solution containing 0.16 to 100 µM of N'-(2-phenoxypyridine-3-carbonyl)-3-(trifluoromethyl)benzhydrazide (Example 1) or other test compound (0.016 to 10 µM final). An aliquot of 22.5 µl of cells was added to a well of a 384-well microtiter plate containing 2.5 µl of a 10% DMSO in RPMI-1640 media solution without test compound as the control sample. The samples were mixed by agitation and then incubated at 37° C. for 48 h in a 5% CO$_2$-95% humidity incubator. After incubation, the samples were removed from the incubator and 25 µl of a solution containing 14 µM of N-(Ac-DEVD)-N'-ethoxycarbonyl-R110 (SEQ ID No: 1) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated at room temperature. Using a fluorescent plate reader (Model SpectraMax Gemini, Molecular Devices), an initial reading (T=0) was made approximately 1–2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$$RFU_{(T=3h)} - \text{Control } RFU_{(T=0)} = \text{Net } RFU_{(T=3h)}$$

The activity of caspase cascade activation was determined by the ratio of the net RFU value for N'-(2-phenoxypyridine-3-carbonyl)-3-(trifluoromethyl)benzhydrazide (Example 1) or other test compound to that of control samples. The $EC_{50}$ (nM) was determined by a sigmoidal dose-response calculation (Prism 2.0, GraphPad Software Inc.). The caspase activity (Ratio) and potency ($EC_{50}$) are summarized in Table I:

TABLE I

Caspase Activity and Potency

| Example # | T-47D Ratio | T-47D $EC_{50}$ (nM) | ZR-75-1 Ratio | ZR-75-1 $EC_{50}$ (nM) |
|---|---|---|---|---|
| 1 | 11.6 | 464 | 1.8 | INACTIVE |
| 8 | 7.3 | 744 | 5.6 | 728 |

Thus, N'-(2-phenoxypyridine-3-carbonyl)-3-(trifluoromethyl)-benzhydrazide (Example 1) and N'-(2-phenoxypyridine-3-carbonyl)-2-hydroxybenzhydrazide (Example 8) are identified as potent caspase cascade activators and inducer of apoptosis in solid tumor cells.

EXAMPLE 44

Identification of N'-(2-Phenoxypyridine-3-carbonyl)-3-(trifluoromethyl)benzhydrazide and Analogs as Antineoplastic Compound that Inhibits Cell Proliferation ($GI_{50}$)

T-47D and ZR-75-1 cells were grown and harvested as in Example 43. An aliquot of 90 μl of cells ($2.2 \times 10^4$ cells/ml) was added to a well of a 96-well microtiter plate containing 10 μl of a 10% DMSO in RPMI-1640 media solution containing 1 nM to 100 μM of N'-(2-phenoxypyridine-3-carbonyl)-3-(trifluoromethyl)benzhydrazide (0.1 nM to 10 μM final). An aliquot of 90 μl of cells was added to a well of a 96-well microtiter plate containing 10 μl of a 10% DMSO in RPMI-1640 media solution without compound as the control sample for maximal cell proliferation ($A_{Max}$). The samples were mixed by agitation and then incubated at 37° C. for 48 h in a 5% $CO_2$-95% humidity incubator. After incubation, the samples were removed from the incubator and 20 μl of CellTiter 96 $AQ_{UEOUS}$ One Solution Cell Proliferation™ reagent (Promega) was added. The samples were mixed by agitation and incubated at 37° C. for 2–4 h in a 5% $CO_2$-95% humidity incubator. Using an absorbance plate reader (Model 1420 Wallac Instruments), an initial reading (T=0) was made approximately 1–2 min after addition of the solution, employing absorbance at 490 nm. This determines the possible background absorbance of the test compounds. No absorbance for N'-(2-phenoxypyridine-3-carbonyl)-3-(trifluoromethyl)benzhydrazide was found at 490 nm. After the 2–4 h incubation, the samples were read for absorbance as above ($A_{Test}$).

Baseline for $GI_{50}$ (dose for 50% inhibition of cell proliferation) of initial cell numbers were determined by adding an aliquot of 90 μl of cells or 90 μl of media, respectively, to wells of a 96-well microtiter plate containing 10 μl of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 20 μl of CellTiter 96 $AQ_{UEOUS}$ One Solution Cell Proliferation™ reagent (Promega) was added. The samples were mixed by agitation and incubated at 37° C. for 2–4 h in a 5% $CO_2$-95% humidity incubator. Absorbance was read as above, ($A_{Start}$) defining absorbance for initial cell number used as baseline in $GI_{50}$ determinations.

Calculation:

$GI_{50}$ (dose for 50% inhibition of cell proliferation) is the concentration where $[(A_{Test}-A_{Start})/(A_{Max}-A_{Start})]=0.5$ The $GI_{50}$ (nM) are summarized in Table II:

TABLE II $GI_{50}$ in Cancer Cells

| Cell lines | Example 1 $GI_{50}$ (nM) | Example 8 $GI_{50}$ (nM) | Example 15 $GI_{50}$ (nM) |
|---|---|---|---|
| T-47D | 200 | 1000 | 60 |
| ZR-75-1 | 4500 | 300 | 2000 |

Thus, N'-(2-phenoxypyridine-3-carbonyl)-3-(trifluoromethyl)-benzhydrazide (Example 1), N'-(2-phenoxypyridine-3-carbonyl)-2-hydroxybenzhydrazide (Example 8) and 2-phenoxypyridine-3-carboxylic acid (3-trifluoromethyl-benzylidene)-hydrazide (Example 15) are identified as antineoplastic compounds that inhibit cell proliferation.

EXAMPLE 45

Treatment with of N'-(2-Phenoxypyridine-3-carbonyl)-3-(trifluoromethyl)benzyhydrazide Leads to Cell Cycle Arrest and Apoptosis in T-47D Cells T-47D, a breast cancer cell line, was maintained and harvested as described in Example 43. $5 \times 10^5$ Cells were treated with 1 μM of N'-(2-phenoxypyridine-3-carbonyl)-3-(trifluoromethyl)benzhydrazide for 24 h at 37° C. As a control, cells were also incubated with equivalent amount of solvent (DMSO). Cells were harvested at 1,200 rpm and then transferred to 12×75 mm polystyrene tubes. Cells were then resuspended in 500 μl of 1% Na Citrate, 0.1% Triton X-100, and 50 μg/ml of propidium iodide and incubated at room temperature for 30 min followed by flow cytometer analysis. All flow cytometry analyses were performed on FACScalibur (Becton Dickinson) using Cell Quest analysis software. The x-axis plotted the amount of fluorescence and the y-axis is plotted the number of cells with the indicated fluorescence. The T-47D control cell population profile is seen in FIG. 1A and the increase in G2/M (M4) DNA content cells that were treated with N'-(2-phenoxypyridine-3-carbonyl)-3-(trifluoromethyl)benzhydrazide is seen in FIG. 1B.

EXAMPLE 46

Identification of N'-(2-Phenoxypyridine-3-carbonyl)-3-(trifluoromethyl)benzyhydrazide and Analogs as Antineoplastic Compound that Selectively Inhibits the Proliferation of Breast Cancer Cells ($GI_{50}$)

T-47D, ZR-75-1, MX-1, SK-Br-3, MCF-7, Panc-1, K562 and PC-3 cells were grown according to the conditions recommended by American Type Culture Collection. SW620 and NCI-H23 were grown according to the conditions provided by National Cancer Institute. The cell proliferation assay and the calculations of $GI_{50}$ were performed as in Example 21 (Tables III and IV).

TABLE III $GI_{50}$ in breast cancer cell lines.

| | $GI_{50}$(nM) | | |
|---|---|---|---|
| Cell Line | Example 1 | Example 8 | Example 15 |
| T47D | 200 | 600 | 80 |
| ZR 75-1 | 4500 | 300 | 2000 |
| MCF-7 | 400 | 800 | 250 |
| MX-1 | 400 | 1000 | 400 |
| SK-Br-3 | 40 | 300 | 20 |

TABLE IV $GI_{50}$ in non-breast cancer cell lines.

| | $GI_{50}$(nM) | | |
|---|---|---|---|
| Cell Line | Example 1 | Example 8 | Example 15 |
| PC-3 | >10,000 | Not done | ND |
| Panc-1 | >10,000 | Not done | ND |
| SW-620 | >10,000 | 1000 | >10,000 |
| NCI-H23 | >10,000 | 1000 | >10,000 |
| K562 | >10,000 | 450 | ND |

Thus, N'-(2-phenoxypyridine-3-carbonyl)-3-(trifluoromethyl)-benzhydrazide (Example 1) and 2-phenoxypyridine-3-carboxylic acid (3-trifluoromethyl-benzylidene)-hydrazide (Example 15) were identified as antineoplastic compounds that selectively inhibits the growth of breast cancer cells. N'-(2-Phenoxypyridine-3-carbonyl)-2-hydroxybenzhydrazide (Example 8) was found to be an antineoplastic compound inhibiting the growth of both breast and non-breast cancer cells.

EXAMPLE 47

N'-(2-phenoxypyridine-3-carbonyl)-3-(trifluoromethyl)benzhydrazide Inhibits the Clonogenic Survival of T47D and MX-1 Solid Tumor Cell Lines T47D and MX-1 cells were grown according to the conditions recommended by American Type Culture Collection. In a well of a 96 well plate, 30,000 cells were seeded and treated with compound at the indicated concentrations for 48 hr in a 5% $CO_2$-95% humidity incubator at 37° C. Control wells were treated with the same amount of solvent (DMSO) as the compound samples. After the indicated treatment time, the supernatant was removed to a sterile culture tube and the wells washed with phosphate buffered saline, and the adherent cells trypsinized for 5 min. The trypsinzed cells were added to the culture supernatant, cells were collected (1,200 rpm, 10 min), washed with phosphate buffered saline, and resupended in fresh media. The cells were counted for trypan blue negative cells, and the cells diluted with fresh media to 1,000 cells/ml. To a well of a 24-well plate, 0.1 ml of the cell suspension was added along with 1 ml of fresh media (cell suspensions were passed through a 22G needle several times just before plating to form single cell suspensions). Plates are incubated in a 5% $CO_2$-95% humidity incubator at 37° C. for 7–10 days. Colonies are counted when the sizes reached greater than 50 cells per colony. Cells are washed with phosphate buffered saline, fixed with 100% methanol for 15 min, and then stained with 0.5% gentian violet for 15 min. Colonies are rinsed with water and the colonies counted and the fraction surviving expressed as the percentage of the number of control colonies.

The results showed that after a 48 hr treatment, N'-(2-phenoxypyridine-3-carbonyl)-3-(trifluoromethyl)benzhydrazide (Example 1) inhibited the ability of T47D and MX-1 cells to proliferate and their colony forming ability with an $IC_{50}$ of about 1050 and 600 nM, respectively (FIG. 2).

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having the formula V:

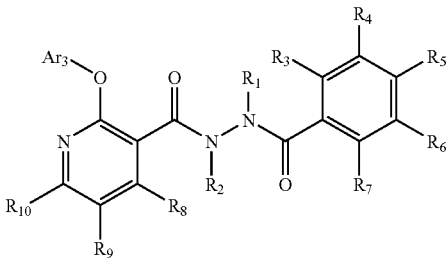

or a pharmaceutically acceptable salt thereof, wherein:

$Ar_3$ is optionally substituted aryl;

$R_1$ and $R_2$ are independently hydrogen, alkyl or cycloalkyl;

$R_3$–$R_{10}$ are independently hydrogen, halo, haloalkyl, aryl, fused aryl, carbocyclic, alkyl, alkenyl, alkynyl, aralkyl, arylalkenyl, arylalkynyl, carbocycloalkyl, hydroxyalkyl, nitro, amino, cyano, acylamino, hydroxy, thiol, sulfonyl, phosphonyl, acyloxy, azido, alkoxy, aryloxy, arylalkoxy, haloalkoxy, carboxy, carbonylamido or alkylthiol;

with the proviso that when $Ar_3$ is unsubstituted phenyl then each of $R_3$–$R_7$ is other than $NH_2$, $NHCH_3$, $NO_2$, halo or $CF_3$ and at least one of $R_3$–$R_7$ is other than hydrogen;

wherein the alkyl, alkoxy, alkenyl and alkynyl groups may have optional substituents selected from the group consisting of one or more halo, hydroxy, carboxyl, amino, nitro, cyano, $C_1$–$C_6$ acylamino, $C_1$–$C_6$ acyloxy, $C_1$–$C_6$ alkoxy, aryloxy, alkylthio, $C_6$–$C_{10}$ aryl, $C_4$–$C_7$ cycloalkyl, $C_2$–$C_6$ alkenyl, $C_2$–$C_6$ alkynyl, $C_6$–$C_{10}$ aryl $(C_2$–$C_6)$alkenyl and $C_6$–$C_{10}$ aryl$(C_2$–$C_6)$alkynyl groups; and wherein the aryl, aralkyl, aralkenyl and aralkynyl groups may have optional substituents selected from the group consisting of one or more halo, $C_1$–$C_6$ haloalkyl, $C_6$–$C_{10}$ aryl, $C_6$–$C_{10}$ aryloxy, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl $(C_1$–$C_6)$alkyl, $C_6$–$C_{10}$ aryl$(C_2$–$C_6)$alkenyl-, $C_6$–$C_{10}$ aryl$(C_2$–$C_6)$alkynyl, $C_1$–$C_6$ hydroxyalkyl, nitro, amino, ureido, cyano, $C_1$–$C_6$ acylamino, hydroxy, thiol, $C_1$–$C_6$ acyloxy, azido, $C_1$–$C_6$ alkoxy and carboxy groups.

2. The compound of claim 1, wherein $R_1$ and $R_2$ are hydrogen.

3. The compound of claim 1, wherein $Ar_3$ is optionally substituted aryl.

4. The compound of claim 4, wherein $Ar_3$ is optionally substituted phenyl.

5. The compound of claim 1, wherein said compound is selected from the group consisting of:

N'-[2-(4-Methylphenoxy)pyridine-3-carbonyl]-2-hydroxy-benzhydrazide;

N'-[2-(4-Methylphenoxy)pyridine-3-carbonyl]-3-(trifluoromethyl)benzhydrazide;

N'-(2-Phenoxypyridine-3-carbonyl)-3-hydroxybenzhydrazide;

N'-(2-Phenoxypyridine-3-carbonyl)-4-hydroxybenzhydrazide;

N'-(2-Phenoxypyridine-3-carbonyl)-2-hydroxybenzhydrazide; and pharmaceutically acceptable salts thereof.

6. A pharmaceutical composition, comprising the compound of claim 1, and a pharmaceutically acceptable carrier.

7. The pharmaceutical composition of claim 6, wherein $R_1$ and $R_2$ are hydrogen.

8. The pharmaceutical composition of claim 6, wherein at least one of $R_3$–$R_7$ is other than hydrogen.

9. The pharmaceutical composition of claim 6, wherein $Ar_3$ is optionally substituted phenyl.

10. The pharmaceutical composition of claim 9, wherein said compound is selected from the group consisting of:

N'-[2-(4-Methylphenoxy)pyridine-3-carbonyl]-2-hydroxy-benzhydrazide;

N'-[2-(4-Methylphenoxy)pyridine-3-carbonyl]-3-(trifluoromethyl)benzhydrazide;

N'-(2-Phenoxypyridine-3-carbonyl)-3-hydroxybenzhydrazide;

N'-(2-Phenoxypyridine-3-carbonyl)-4-hydroxybenzhydrazide;

N'-(2-Phenoxypyridine-3-carbonyl)-2-hydroxybenzhydrazide; and a pharmaceutically acceptable salts thereof.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Fluorogenic substrate

<400> SEQUENCE: 1

Asp Glu Val Asp
1
```